United States Patent
Timm et al.

(10) Patent No.: US 7,223,228 B2
(45) Date of Patent: May 29, 2007

(54) URETHRAL OCCLUSIVE ASSEMBLY FOR PREVENTING URINARY INCONTINENCE

(75) Inventors: Gerald W. Timm, Minneapolis, MN (US); David W. Anderson, Brooklyn Park, MN (US)

(73) Assignee: GT Urological, LLC, Minneapolis, MN (US)

( * ) Notice: Subject to any disclaimer, the term of this patent is extended or adjusted under 35 U.S.C. 154(b) by 0 days.

(21) Appl. No.: 11/122,827

(22) Filed: May 5, 2005

(65) Prior Publication Data

US 2005/0267324 A1   Dec. 1, 2005

Related U.S. Application Data

(60) Provisional application No. 60/569,420, filed on May 7, 2004, provisional application No. 60/600,613, filed on Aug. 11, 2004.

(51) Int. Cl.
 *A61F 2/02* (2006.01)
(52) U.S. Cl. .......................................................... 600/30
(58) Field of Classification Search ............ 600/29–31, 600/37, 40; 128/DIG. 25, 897, 898
 See application file for complete search history.

(56) References Cited

U.S. PATENT DOCUMENTS

| 3,419,008 | A |   | 12/1968 | Plishner |
| 3,924,631 | A | * | 12/1975 | Mancusi, Jr. ................ 600/30 |
| 3,926,175 | A |   | 12/1975 | Allen et al. |
| 3,939,821 | A |   | 2/1976  | Roth |
| 4,024,855 | A |   | 5/1977  | Bucalo |
| 4,994,019 | A | * | 2/1991  | Fernandez et al. ............ 600/30 |
| 5,184,629 | A |   | 2/1993  | Erickson et al. |
| 5,453,079 | A |   | 9/1995  | Schwaninger |
| 5,526,803 | A |   | 6/1996  | Kelly |
| 5,762,599 | A |   | 6/1998  | Sohn |
| 5,997,467 | A |   | 12/1999 | Connolly |
| 6,171,231 | B1 |  | 1/2001  | Connolly |
| 6,234,174 | B1 |  | 5/2001  | Cheng et al. |
| 6,289,895 | B1 |  | 9/2001  | Cheng et al. |
| 6,319,191 | B1 |  | 11/2001 | Sayet et al. |
| 6,349,727 | B1 |  | 2/2002  | Stewart, Jr. |
| 6,409,656 | B1 |  | 6/2002  | Sangouard et al. |
| 6,463,932 | B1 |  | 10/2002 | Single et al. |
| 6,540,665 | B1 |  | 4/2003  | Connolly |
| 6,609,522 | B2 |  | 8/2003  | Cheng et al. |
| 2002/0185138 | A1 | | 12/2002 | Single et al. |

OTHER PUBLICATIONS

PCT/US2005/015971 International Search Report.

(Continued)

*Primary Examiner*—Samuel G. Gilbert
(74) *Attorney, Agent, or Firm*—Hamre, Schumann, Mueller & Larson, P.C.

(57) ABSTRACT

A urethral occlusive assembly includes an implant component and external component. The implant component includes a flexible bridge member connecting two opposed implant supports. The implant component is implanted about a dorsal surface of an animal urethra. An external component is disposed external to and proximate the animal urethra. The external component operatively communicates with the implant component to transmit a compressive load on the urethra. By communication between the implant and external components, either the implant component or the external component actively compresses the urethra against the flexible bridge member, thereby effecting urinary continence.

20 Claims, 16 Drawing Sheets

OTHER PUBLICATIONS

"An Implantable Incontinence Device", Gerald W. Timm, J. Biomechanics, vol. 4, pp. 213-219, 1971.

"Treatment of Urinary Incontinence by an Implantable Prosthetic Urinary Sphincter", Scott et al.. The Journal of Urology, vol. 112, Jul. 1974, pp. 75-80.

"Mayo Clinic Long-Term Analysis of the Functional Durability of the AMS 800 Artificial Urinary Sphincter: A Review of 323 Cases". Elliott et al., The Journal of Urology, vol. 159, Apr. 1998, pp. 1206-1208.

"Male Slings for Postprostatectomy Incontinence", Cespedes et al., Technologies in Urology, vol. 7, No. 2. 2001, pp. 176-183.

"Modified Bulbar Urethral Sling Procedure for the Treatment of Male Sphincteric Incontinence", Kapoor et al., Journal of Endourology, vol. 15, No. 5. Jun. 2001. pp. 545-549.

"Radical Prostatectomy: Prospective Assessment of Mortality and Morbidity", Davidson et al., European Urology, Clinical Paper, 1996;29: 168-173.

"Comparison of Artificial Urinary Sphincter and Collagen for the Treatment of Postprostatectomy Incontinence", Kuznetsov et al., Adult Urology, May 30, 2000, pp. 600-603.

"A Magnetic Device for increasing the urethral resistance to flow: an experimental study in female dogs", Ali-El-Dein et al., Urology & Nephrology. Center, 2000 BJU International, vol. 85, No. 1, Jan. 2000. pp. 150-154.

"A Magnetic Urethral Closure Device: Preliminary Report of an Experimental Study", Gruneberger et al., The Journal of Urology, vol. 130, Oct. 1983, pp. 798-801.

"Development of a magnetic urethral closure device- an experimental study", Gruneberger et al., Zentraibl Gynakol 115 (1993), pp. 328-331. (Abstract/Summary in English).

"A Magnet System for Urethral Closure in Females", Gruneberger et al., Department of Gynaecology and Obsteretrics. J. Biomed Eng., vol. 6, Apr. 1984, pp. 102-106.

"AMS 800 Urinary Control System", (overview) AMS Solutions for Life, 2005. American Medical Systems.

"InVance Male Sling", (overview), AMS Solutions for Life. 2005, Amercian Medical Systems.

* cited by examiner

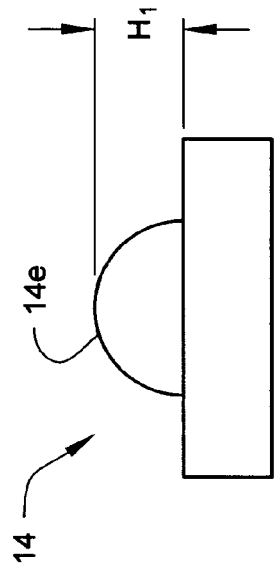
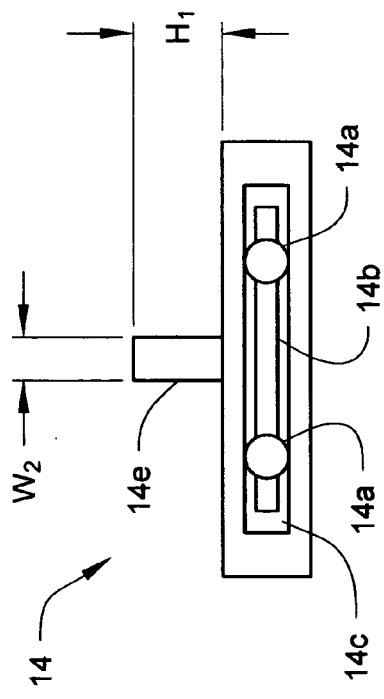
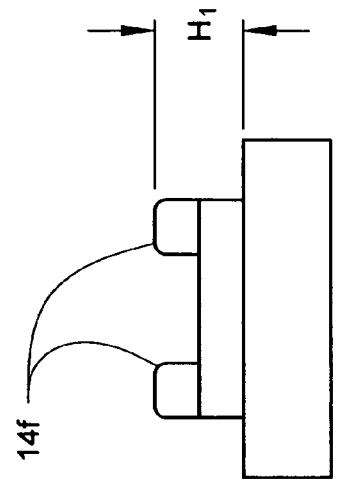
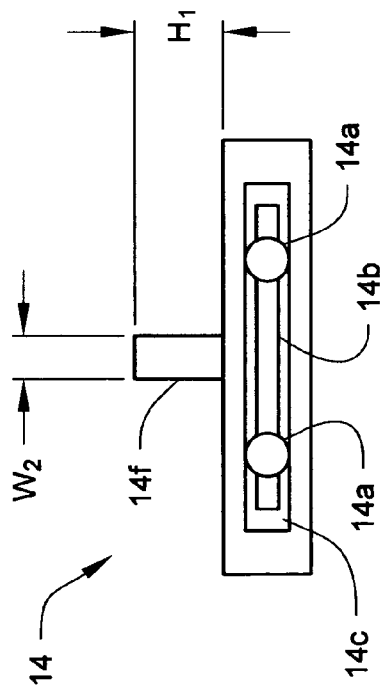

URETHRAL OCCLUSIVE ASSEMBLY FOR PREVENTING URINARY INCONTINENCE

CROSS-REFERENCE TO RELATED APPLICATIONS

The present application draws priority from U.S. Provisional Patent Application Ser. Nos. 60/569,420 and 60/600,613, both entitled "Magnetic Urethral Occlusive Device," and both of which are incorporated herewith by reference in their entirety.

This invention was made with government support under SBIR Grant Number 1R43DK066941-01A2 awarded by the National Institutes of Health. The government has certain rights in the invention.

FIELD OF THE INVENTION

The invention relates to a urethral occlusive device for preventing urinary incontinence. More particularly, the invention relates to a urethral occlusive assembly and method for the same employing an implant component operatively communicating with an external component, whereby one of the implant or external components actively compresses a patient's urethra to prevent urinary incontinence.

BACKGROUND OF THE INVENTION

Urethral occluding devices are well known and widely used to prevent urinary incontinence. In particular, a variety of external penile clamps and implanted devices have been proposed for solving urinary leakage problems. Typically, such devices have been employed for use in the inspection and treatment of diseases, wounds and other abnormal conditions of the bodies of humans and lower animals.

The Artificial Urinary Sphincter (AUS 800) is produced by American Medical Systems. The AUS 800 is a totally implantable hydraulic sphincter implanted in both males and females experiencing urinary incontinence. A silicone pressure regulating balloon, silicone control pump, and silicone urethral occlusive cuff are packaged separately for implant. In males for example, an incision is made in the perineum, and a bulbous urethral dissection is performed. The cuff is filled with saline or contrast media and placed around the urethra. The control pump also is filled with saline or contrast media, and placed within the scrotum through this same incision. The pressure regulating balloon is placed into the prevesical space through an additional incision made in the abdomen. Tubing, emanating from each component is routed between incisions and appropriate connections are made. The device is deactivated for a period of approximately six weeks to allow tissue healing to proceed and urethral edema to subside.

At activation, the control pump is squeezed sharply to unseat a puppet and open operational fluid flow paths. The AUS 800 provides a urethral occlusive state. The patient is taught to operate the device by squeezing the control pump through the scrotal skin. This action transfers fluid from the cuff to the pressure regulating balloon. The balloon forces the fluid through a fluid restrictor and back into the cuff to reestablish an occlusive urethral pressure within three to five minutes.

The AUS 800 is a complicated device to implant. The requirement of multiple components and the required intraoperative techniques make it prone to component failure. Some common failures include infection, urethral erosion and atrophy leading to increased urine leakage. Additionally, fluid leaks due to tubing disconnection, intraoperative punctures, and silicone wear within the silicone urethral cuff folds are also causes of device failure.

Urethral and bladder neck slings have long been used in the treatment of female incontinence, but are infrequently used for male urinary incontinence. In the male for example, a perineal or abdominal incision is made and titanium bone screws are place in the pelvic bone. A synthetic or biologic sling material is attached to the screws, which elevate the urethra or bladder neck, thereby applying a compressive force to stop urine leakage.

Studies of autologous tissue slings mention infection and urinary retention requiring intermittent self catheterization, as complications in some patients.

Furthermore, others have employed external penile clamps. The Cunningham clamp, for example, provides a padded, hinged clamp with a latch used to compress the penis. For the clamp to be effective, however, imparts large clamping forces on the penis that often lead to pain, swelling and penile skin break down.

The C3 clamp disclosed in U.S. Pat. No. 5,184,629 provides a clamp intended for use that is limited to approximately one week. The C3 is constructed from a co-extruded and thermoformed polyolefin sheet. The resultant component has two clam shelled halves connected by a hinge. The penis is placed through a portal between the two halves and the halves are folded over to compress the penis. The clam shells are held closed by a Velcro® strap. Force is localized on the urethra by presence of a raised bump on the bottom clam shell half. However, the C3 is available in only two fixed sizes. As there is great penile anatomical variation requiring multiple clamp sizes, it may be frequent that an improper clamp is selected. Further, the ability to operate the strapping system is often difficult for older, arthritic men. Such inconsistencies in sizing and the user dependent strapping system, however, make the C3 less reliable in its ability to control leakage.

Still, others have employed male external (condom) catheters (MEC). These catheters are rolled onto the penis, like a typical condom, and have a specially designed funnel end that connects to a collection device, usually a leg drainage bag. These devices are available in a variety of adhesive application methods due to differences in patient skin sensitivity, changes in penis size during wearing time, penile retraction and manual dexterity. The MEC is typically replaced every twenty-four hours. Difficulties with the MEC include skin sensitivity to materials, tissue sloughing due to the constantly wet environment, manual dexterity required for application, leakage due to adhesive release, and change in penis size during wearing time and penile retraction.

Urethral bulking agents have been injected into the area around the urethra to augment or bulk the sphincter enabling it to coapt and close.

Bulking agents are either synthetic or biologically derived. Biologically derived bulking agents include injections of a patient's own fat cells, polysaccharides or bovine collagen. The body tends to resorb these substances over time, and reinjection over time must be performed. Some synthetic bulking agents, may not be resorbed, but are prone to migrate and reduce coaptation of the urethra. Some of these products may consist of a balloon, which can be reinflated periodically to accommodate changes in continence status, thereby obviating the problems of resorption and migration. Urethral bulking agents have been used extensively in women. However, the performance of injectables in men has not met expectations, and is not widely used. Only 2% to 21% total continence and 19% to 35% improved continence was reported in studies of collagen injections in men.

While these previous applications have provided some advancement for controlling urinary dysfunction and protecting against bladder malfunction, improvements may yet be made to a urethral occlusive assembly for females and males experiencing stress urinary incontinence. There is need for a urethral occlusive assembly that provides optimum comfort and that is convenient for use, while sufficiently preventing urinary leakage. Improvements may still be made to a urethral occlusive assembly that prevents tissue necrosis.

SUMMARY OF THE INVENTION

It is the purpose of the present invention to overcome these difficulties, thereby providing an improved urethral occlusive assembly. The present invention provides a surgical cure for stress urinary incontinence in males and females. The urethral occlusive assembly includes an implant component disposed on a male or female patient urethra, and includes an external component placed external to a user's body. The implant component operatively communicates with the external component to compress a male or female urethra and effect urinary continence.

In one preferred embodiment, only one of the implant component or external component actively compresses the patient's urethra. Preferably, the implant component laterally compresses the urethra, or the external component compresses the urethra by imparting an external load on the urethra to compress the urethra against the implant component.

In one embodiment, this may be accomplished by providing an implant component that includes implant magnets disposed around the male or female urethra. An external component includes at least one external magnet placed external to a user's body. Attraction of the implant magnets to the external magnet(s) compresses the urethra against a portion of the implant component, thereby to control of urine leakage.

One embodiment of the urethral occlusive assembly includes a pair of rare earth magnets implanted on each side of the male or female urethra. The implant magnets are joined by a flexible bridge member. An external magnet or magnets are disposed proximate the urethra. Attraction of the external magnet(s) to the implant magnets causes urethral compression against the flexible bridge member. This increases urethral luminal pressure and prevents inadvertent urine leakage encountered by men and women with urinary stress incontinence.

When attracted to the implant magnets, the external magnet(s) enable the external component to actively compress the urethra against the flexible bridge member. The external magnet(s) may be held in place under its attractive force to the implanted magnets. The external magnet(s) may also be held in place by an external securing member, such as a flexible or rigid clamp to prevent dislodgement due to bodily movement.

In another embodiment, the external component includes an external urethral occluding member. The external magnet(s) aid in locating and holding the occluding member in place against a surface proximate and external to the urethra. The occluding member actively localizes compression on the urethra and against the flexible bridge member.

In another embodiment, the external magnet(s) may be disposed on an external magnet support. In one preferred embodiment, the external magnet(s) and support are housed within a sleeve, and may be held in place through an attractive force with the implant magnets.

In another embodiment of a urethral occlusive assembly, an implant component includes a pair of rare earth magnets implanted on each side of the male or female urethra. These magnets are joined by a flexible bridge member. The external component includes a pair of magnets external to the body attracted to the implanted magnets. By varying the spacing between the external magnet pair, the spacing of the implant magnet pair may be varied. As the spacing of the implant magnet pair is decreased, the urethra is actively compressed by the two implant magnets, and the urethra is occluded to prevent urine leakage.

Another embodiment of an external component includes a flexible web portion. The flexible web portion is disposed along the body of a magnet support. The flexible web enables the magnet support to articulate on an outer tissue proximate the urethra.

In another embodiment of the external component, the magnet support includes a removable spacer disposed thereon. The removable spacer is positioned proximately to the implant component. The dimensions of the removable spacer may be varied to alter the compression load, such as by varying the distance between the implant magnets and the external magnet(s).

In yet another embodiment of an external component, a single topically applied magnet is employed to enable the external component to actively compress the urethra.

In another embodiment of an external component, the magnetic strength of the external magnet(s) may be increased thereby increasing urethral compression. To effect a desired urethral compression load, a stronger magnet may be employed rather than a weaker one or vice versa.

In yet another embodiment, the external component provides the external magnet(s) being disposed within the magnet support at varying separation distances from the implant magnets. In this configuration, the increase/decrease of the separation distance between the implant and external magnets respectively determines the decrease/increase of urethral compression load.

In yet another embodiment of an external component, a recess is disposed on the external magnet support. Such a recess enables expansion of the urethra and contacting skin to expand into the recess. In this configuration, tissue necrosis and user discomfort can be prevented when the urethra is actively compressed by the implant component.

In yet another embodiment of a urethral occlusive assembly for a male, an implant component does not employ magnets. In this configuration, a non-magnetic implant is disposed around a male urethra. An external securing member is applied around the penis to compress the same. The compression by the external securing member is imparted to the non-magnetic implant, which actively compresses the urethra to prevent urine leakage.

The urethral occlusive assembly provides several features and advantages. Urethral compression may be adjusted without additional surgery to accommodate changing degrees of incontinence. This may be accomplished through application of external magnets of varying strengths or the selection of different urethral occluder geometries. This non-surgical adjustability is not available with the AUS 800 or male slings.

The present invention provides the ability to periodically remove the external magnet and hence the occlusive pressure from the urethra and penis, so as to minimize urethral atrophy and erosion.

The present invention provides removal and re-application of the external magnet by the user, so that voiding urine from the body is a simple, convenient procedure. The need to locate and pump an implanted component, as with the AUS 800, is eliminated. Further, there is no abdominal straining required to void urine, as typically required with urethral slings.

The urethral occlusive assembly of the present invention provides a simple, one-piece, implant component not prone to wear and subsequent fluid leakage as with the AUS 800.

The urethral occlusive assembly may be implanted using a single implant incision with uncomplicated penile urethral dissection as opposed to a minimum of two incisions required to implant the AUS 800.

These and other various advantages and features of novelty, which characterize the invention, are pointed out in the following detailed description. For better understanding of the invention, its advantages, and the objects obtained by its use, reference should also be made to the drawings which form a further part hereof, and to accompanying descriptive matter, in which there are illustrated and described specific examples of an apparatus in accordance with the invention.

BRIEF DESCRIPTION OF THE DRAWINGS

Like reference numbers generally indicate corresponding elements in the Figures. The embodiments illustrated are exemplary only and are in accordance with the principles of the present invention.

FIG. 5A represents an elevated side view of another embodiment of a sleeve of the external component.

FIG. 5B represents another elevated side view of a sleeve of the external component of FIG. 5A.

FIG. 6A represents an elevated side view of yet another embodiment of a sleeve of the external component.

FIG. 6B represents another elevated side view of the sleeve of FIG. 6A.

DETAILED DESCRIPTION OF THE PREFERRED EMBODIMENT

Figure 1A:
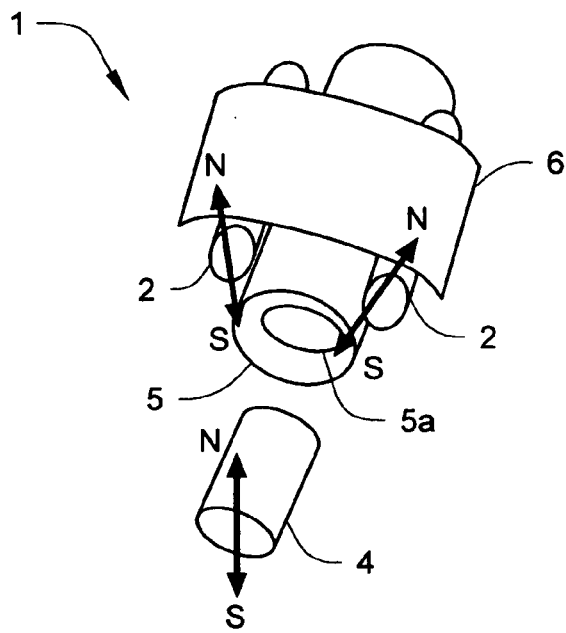
FIG. 1A represents an elevated perspective view of one embodiment of a urethral occlusive assembly.

One embodiment of a urethral occlusive assembly 1 is provided in FIGS. 1A–3B. FIGS. 1A and 1C illustrate the urethral occlusive assembly 1 as applied to a male urethra 5, and FIG. 1B shows an embodiment of the urethral occlusive assembly 1 vaginally applied to a female urethra 7.

The urethral occlusive assembly 1 provides an implant component including implant magnets 2 connected with a flexible bridge member 6. The implant component is implanted inside a patient's body and around a male 5 or female urethra 7. Preferably, the implant magnets 2 and bridge member 6 are arranged on a dorsal surface of the male 5 or female urethra 7, such that the implant magnets 2 straddle either urethra.

Figure 1B:
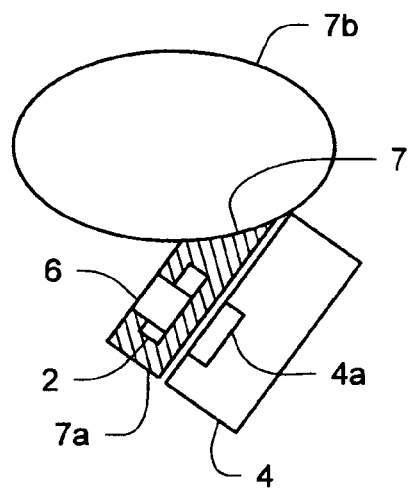
FIG. 1B represents an elevated side plan view of the urethral occlusive assembly of FIG. 1A vaginally applied.
Figure 1C:
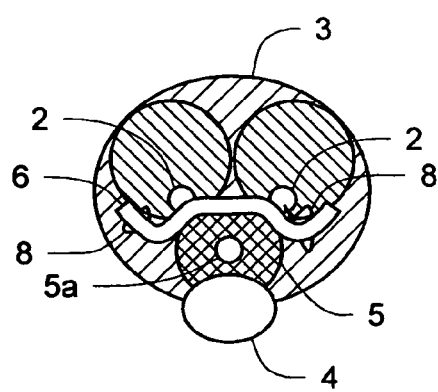
FIG. 1C represents an elevated end view of the urethral occlusive assembly of FIG. 1A as applied to penile tissue shown in section.

The implant component may be secured to surrounding tissue, such as penile tissue of a male urethra 5 (FIG. 1C). In one embodiment, suture attachments 8 preferably fix the flexible bridge member 6 to surrounding penile tissue of the urethra 5.

Preferably, the implant component provides that the implant magnets 2 are disposed parallel to one another by the flexible bridge member 6. The flexible bridge member 6 may be constructed of a material, such as but not limited to, silicone rubber, polyester reinforced silicone sheet, stainless steel or titanium encased in a silicone jacket, or expanded polytetrafluoroethylene (ePTFE) in a silicone jacket.

Lateral extensions of the bridge member 6 may be provided as a means by which the surgeon may anchor the implant component, for instance to the urethral spongiosum or tunica albuniginea in the male and the periurethral tissue in the female. Urethral circumferences within the range of 1 cm to 4.5 cm can be accommodated and multiple sizes for the implant component may be considered.

The urethral occlusive assembly 1 further includes an external component 4. Preferably, the external component 4 may itself be at least one external magnet, or may include a separate external magnet support (further discussed below) containing the external magnet(s) therein.

FIG. 1B illustrates one example in a vaginally applied urethral occlusive assembly 1. The urethral occlusive assembly 1 compresses a urethra 7 to prevent leakage through the urinary pathway 7a from the urinary bladder 7b. The external magnet 4a resides within a support. It will be appreciated that the external component 4 for a male (FIGS. 1A and C) also will include an external magnet (not shown), such as external magnet 4a.

As will be detailed below, only one of the implant component or external component actively compresses the patient's urethra. Preferably, the implant component laterally compresses the urethra, or the external component compresses the urethra by imparting an external load on the urethra to compress the urethra against the implant component.

FIGS. 1A–C illustrates that the external magnet may compress either the male urethra 5 or female urethra 7 against the flexible bridge member 6. In this manner urine leakage may be prevented through pathways 5a, 7a. The external magnet may be held in place under its attractive force to the implant magnets 2. It may also be held in place by a flexible or rigid clamp to prevent dislodgement due to bodily movement (further discussed below).

As shown in FIGS. 1A, 1C for a male, the external magnet of the external component 4 are held in place on an outer skin surface of the penis 3 through attraction to the implant magnets 2. For a female, the external magnet 4a of the external component 4 is held in place at the anterior vaginal wall by its attraction to the implant magnets 2.

Figure 7A:
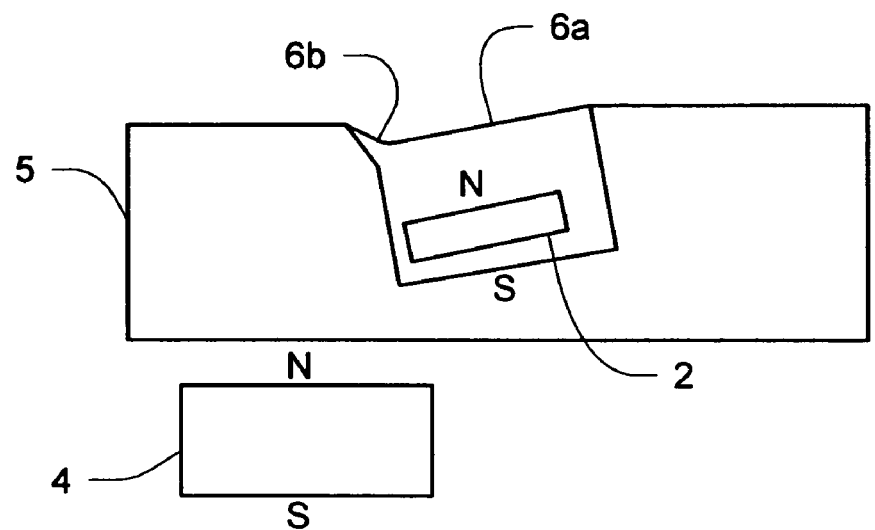
FIG. 7A represents a side schematic view of the urethral occlusive assembly of FIG. 1A.
Figure 7B:
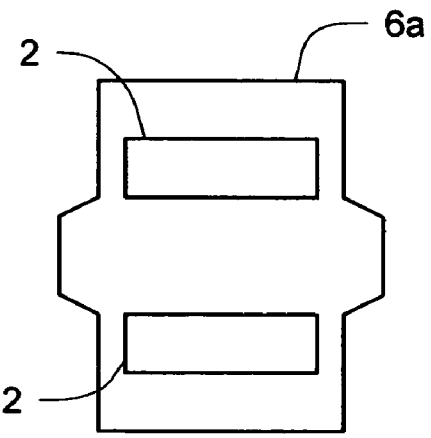
FIG. 7B represents a top plan view of one embodiment of an implant component.

The implant magnet 2 and flexible bridge member 6 may twist relative to the urethral axis. This may occur as a result of preferential attraction of one end of an implant magnet to the external magnet. To prevent urethral damage, FIGS. 7A–B illustrate another embodiment for a flexible bridge member 6a. The flexible bridge member 6a includes a leading edge of the flexible bridge member 6a defining a flex point 6b. Axial extensions of the leading bridge edges may also be made to create a flex point (FIGS. 7B).

The degree of urethral compression may be varied by changing the external magnet 4a strength, or by changing the distance which the external magnet 4a is separated from the penile or vaginal skin. For example, a non-magnetic structure may be included for surrounding the external magnet. An increasing a thickness of a non-magnetic structure increases a distance from, for instance, the penile skin and internal magnet. Such a structure reduces magnetic attractive force between the implant magnets and external magnet, thereby reducing urethral compression. Likewise, decreasing a thickness of a non-magnetic structure increases attractive strength and urethral compression. This is further described below.

Figure 2:
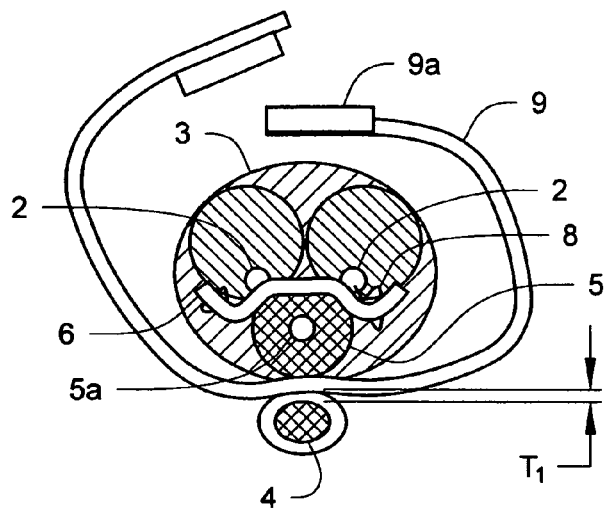
FIG. 2 represents an elevated end view of the urethral occlusive assembly of FIG. 1A further showing one embodiment of an external securing member in a released position.

As shown in FIG. 2, another preferred embodiment of holding the external component 4 on the penis 3 includes an external securing member 9. The external securing member 9 may be a flexible strap, made from materials such as but not limited to woven cotton, polyester fabrics, open or closed celled urethane, or open or closed polyethylene foams. Such an external securing member 9 may also include a closure member 9a. The closure member 9a may be arranged to accommodate a wide variety of penile sizes, and may be constructed of an adhesive or Velcro® closure. It will be appreciated, however, that the embodiment shown is exemplary only. Other configurations and materials for the securing and closure members may be equally or more suitable.

Figure 3A:
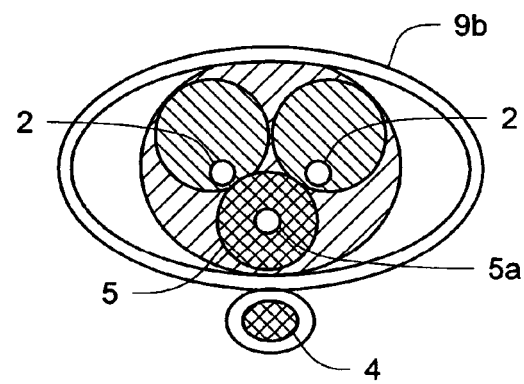
FIG. 3A represents an elevated end view of the urethral occlusive assembly of FIG. 1A further showing another embodiment of an external securing member in a secured position.
Figure 3B:
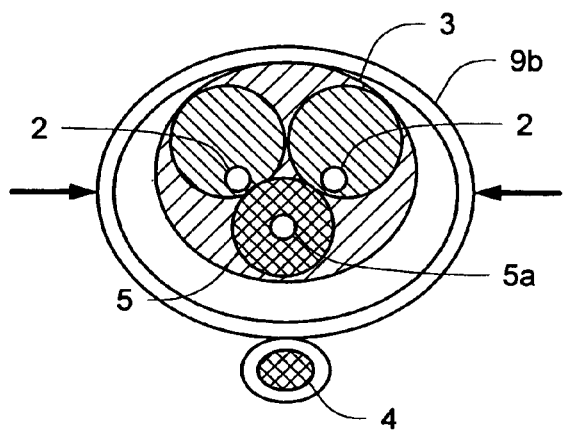
FIG. 3B represents an elevated end view of the urethral occlusive assembly of FIG. 1A showing the external securing member of FIG. 3A in a released position.

In another embodiment of a securing member 9b, a rigid clamping mechanism may alternatively be employed to hold the external component 4 in place. As shown in FIG. 3A–B, the external component 4 may be fixed to the external securing member 9b. Preferably, the external securing member 9b is an enclosed compressible biasing member. Such a biasing member may be compressed to allow insertion of a penis 3 (FIG. 3B), and may be released from its compressed position to bias onto the penis 3 in a relaxed state (FIG. 3A). In the relaxed state, the external securing member 9b conforms to the size of the penis 3 and holds the external component 4 firmly in place.

As shown by the arrow directional of FIG. 3B, the external securing member 9b may be squeezed across its body, such that it deforms and forces the external magnet away from the penis 3. In this configuration, the attraction between implant magnets 2 and external magnet may be reduced thereby allowing unobstructed urinary voiding.

It is anticipated that the varying external securing member 9b sizes below may be employed to accommodate some of the known anatomical variations of the penis. Such sizes may include but are not limited to: 4 cm to 6 cm penile circumferences (medium), 6 cm to 10 cm penile circumferences (large), and 10 cm to 14 cm penile circumferences (extra large).

The external securing member 9b may be a one-piece injection molded or thermoplastically formed component. Thermoplastics such as, but not limited to, Delrin® may be used in this application. It will be appreciated, however, that such materials are exemplary only. Other plastic and non-plastic materials may be employed that are equally or more suitable.

As one exemplary embodiment, the implant magnets 2 and external magnets 4a of the urethral occlusive assembly 1 includes two neodymium iron boron (NdFeB) grade 45 (energy product of 45 MGOe) rod magnets, and magnetized across their diameter. Preferably, a diameter of 0.125" and a length of 0.50" have an appropriate magnetic attractive strength. Such magnets are readily produced, for example by Magstar Technologies, Inc. and by Dexter Magnetics, Inc.

More preferably, the magnets may be coated or plated with a precious metal (gold, tantalum, platinum) or di-para-xylene (parylene). Such coatings are intended to prevent magnet corrosion and promote tissue biocompatibility. The magnets, in addition to the above-mentioned plating and coating processes, may be encased in a silicone rubber body intended to promote biocompatibility and retard any corrosive process.

Figure 8:
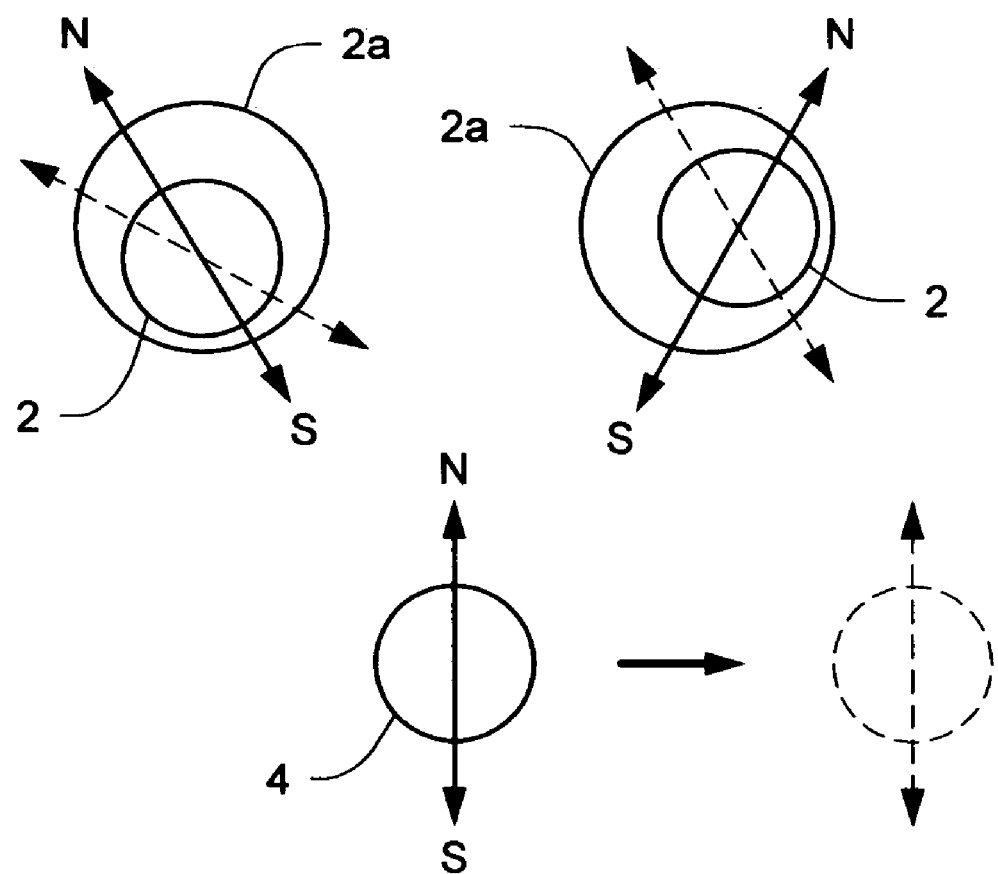
FIG. 8 represents an elevated end view of one embodiment of magnetic member orientation.

As shown in FIG. 8, the implanted magnets 2 each may be contained within a holder 2a. Preferably, the holder 2a resembles a canister to contain the implant magnet 2 therein.

As one example only, a holder 2a may be a 316 LVM stainless steel or 6Al 4V ELI titanium canister, which may be used as an alternative to precious metal plating. Such canisters would be constructed with end caps of the above-mentioned materials, and welded to the canister in an oxygen-free atmosphere to prevent oxidation of the magnets. As FIG. 8 shows, the implant magnets 2 may freely rotate within the holders 2a. This free rotation allows the poles of the implanted magnets 2a to assume the most advantageous position relative to the external magnet 4a in response to inadvertent movement of the external magnet 4a.

As another exemplary alternative, a parylene coating may be employed to provide a low coefficient of friction between the magnet and holder 2a to facilitate free relative rotation.

It will be appreciated, however, that such holders and materials for the same are exemplary only. Other materials may be employed that are equally or more suitable. It will be appreciated that the use of such holders is exemplary only, as holders may or may not be employed as desired for a urethral occlusive assembly 1. As will be further discussed below, the implant magnets 2, for example, may be enclosed within implant supports constructed from any number of the materials above.

Figure 4A:
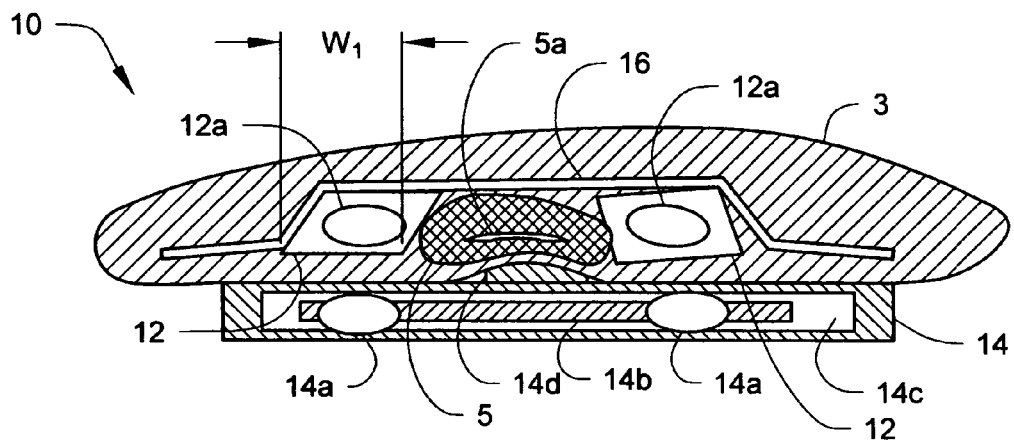
FIG. 4A represents a side sectional view of another embodiment of a urethral occlusive assembly. The assembly is shown in operation for penile urethral compression.
Figure 4B:
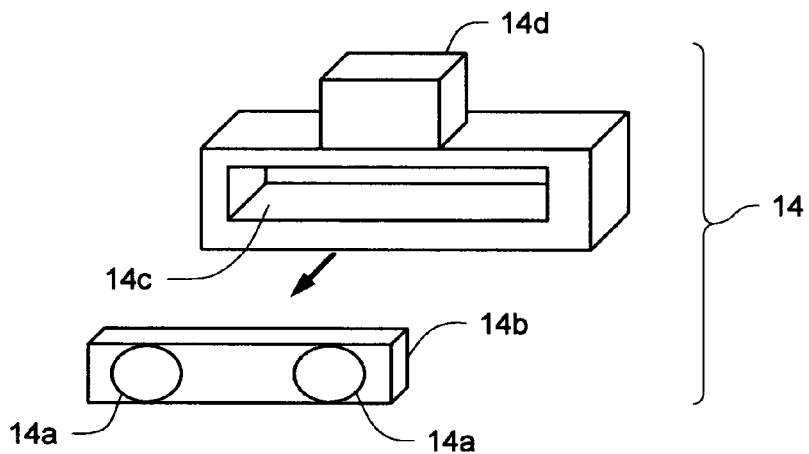
FIG. 4B represents an elevated perspective exploded view of one embodiment of an external component.
Figure 4C:
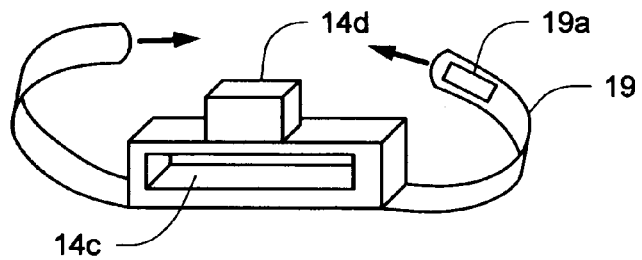
FIG. 4C represents an elevated perspective view of one embodiment of a sleeve of the external component of FIG. 4B.

Alternately, FIGS. 4A–C illustrate another embodiment for a urethral occlusive assembly 10. A modified external component 14 includes external magnets 14a that aid in locating and holding in place an external urethral occluder 14d. The external magnets 14a may be disposed on a magnet support member 14b. As one exemplary embodiment only, the magnet support member 14b is a plate. The external component 14 defines a main body having a sleeve with an opening 14c. The urethral occluder 14d disposed on the main body. Preferably, the opening 14c houses the external magnets 14a and support member 14b.

The urethral occluder 14d may be held in place under its attractive force to the implant magnets 12a. As discussed above, the implant magnets 12a may be enclosed within implant supports 12, so as to protect the magnet material during its implanted state. Preferably, an implant support 12 and implant magnet 12a resemble a capsule structure with the magnet residing therein (further discussed below).

The implant support 12 and implant magnet 12a define a width $W_1$ and length, to maximize a surface area of the tissue compressed between the implant 12a and external 14a magnets. As can be seen by the equation $P=F/A$ where P=tissue pressure, F=magnetic force and A=Area of tissue compression, when the area of tissue compression increases for any given magnetic force, the applied tissue pressure can be reduced proportionately. As one example only, a suitable tissue pressure can be achieved with a width W of 0.25 inches, a length of 0.55 inches, and an attractive force of 0.083 kg. As one preferred example only, a tissue pressure of about 68.9 mm Hg is desired. Such a pressure is below the typical diastolic blood pressure of 80 mm Hg, where blood perfusion is maintained and continued tissue viability is insured.

The urethral occluder 14d may also be held in place by external securing member 19 and closure member 19a. Preferably, the external securing member 19 may be a flexible or rigid clamp as previously described. The external securing member 19 helps prevent dislodgement due to bodily movement when closed by the closure member 19a. The closure member 19a may be constructed as described above.

In operation, the urethral occluder 14d actively compresses the urethra 5 against the flexible bridge member 16 and closes the urinary pathway 5a. This compression occurs when the implant magnets 12a attract the external magnets 14a.

FIG. 4A illustrates urethral compression with respect to a male urethra 5. However, it will be appreciated that the external magnets 14a may also be held on an anterior vaginal wall for holding and positioning a urethral occluder, such as 14d, against a female urethra. The degree of urinary incontinence achieved is determined by the degree of compression between the occluder 14d and the implanted flexible bridge member 16 (See FIG. 4A).

The external magnets 14a are guided to the implant magnets 12a and may be held in place on the penis or vaginal wall by their attraction to the implant magnets 12a. The internal 12a and external 14a magnets have the strength necessary to hold the appropriate attraction to one another.

As one example only, the magnets may be constructed as 0.125" diameter×0.5" long grade 45 NdFeB magnets. Preferably, the external magnets 14a are a reusable parallel pair of grade 45 NdFeB rod magnets (0.125" diameter×0.5" long) magnetized across their diameter. Orientation of the implant and external magnetic poles is such that the magnets are attracted to one another.

Preferably, the separation distance of the implanted magnets 12a is the same as that of the external magnets 14a to insure the greatest possible magnetic attractive strength. Separation distance of the external magnets can be maintained, for example, by encasing them in a magnet support member, such as a reusable thermoplastic plate. FIG. 4B best illustrates the external magnets 14a encased within a magnet support member 14b. Preferably, the thermoplastic plate is injection molded from a material such as but not limited to ABS, polycarbonate, polysulfone or other rigid thermoplastic resin.

The surface of the thermoplastic plate may be marked with a raised visible and or tactile cue indicating the "North Pole" side of the Insert (not shown). To minimize the separation distance between the implant 12a and external 14a magnets, the external magnets 14a may have no plastic extending over their pole surfaces and may be partially exposed (not shown). In such a configuration, the external magnets also may include a plated or parylene coating as described above to prevent oxidative corrosion.

As one example only, the urethral occlusive assembly 10 may be assembled as follows. The external magnets 14a and support member 14b are placed within a disposable external magnet sleeve having an opening 14c and an integral urethral occluder 14d (FIGS. 4B–C). The sleeve may be manufactured from a material such as but not limited to open or closed celled urethane foams, or open or closed celled polyolefin foams. Such a foam may be compression thermoformed or injection molded to obtain the shape of the urethral occluder 14d. As one example only, it has been found that 4 lb polyolefin foams have a structural strength adequate to prevent collapsing when being compressed against the urethra. The use of foam is intended to promote user comfort and to wick away sweat, which may lead to irritation of, for instance, the penile skin.

FIGS. 5A–6B illustrate exemplary embodiments for a urethral occluder, such as 14d. It will appreciated that several shapes may be employed for the urethral occluder to maximize urethral occlusion and protection from urine leakage.

FIGS. 5A–B illustrate a urethral occluder 14e shaped as an arcuate or semi-circular bump with dimensions $W_2$ and $H_1$. The urethral occluder 14e may prevent urine leakage when a bladder pressure of 60 cm $H_2O$ to 70 cm $H_2O$ is exerted.

FIGS. 6A–B illustrate a urethral occluder 14f shaped as a bi-lobed or bumped structure. With reference to penile length, the bi-lobed structure defines that one of the bumps is a proximal or upstream occluding lobe, and the other of the two bumps is a distal or downstream occluding lobe. The urethral occluder 14f also may have a width and height dimensions $W_2$ and $H_1$. It will be appreciated that the dimensions may be substantially similar to that of the urethral occluders 14d, 14e. The urethral occluder 14f may prevent urine leakage when a bladder pressure of 75 cm $H_2O$ to 85 cm $H_2O$ is exerted. The proximal (upstream) lobe provides an initial urethral restriction, which reduces the urine pressure escaping past it. The distal (downstream) lobe provides further urine stream pressure reduction to minimize or eliminate leakage.

It will be appreciated that the width and height dimensions $W_2$ and $H_1$ may be varied for both occluders 14e, 14f as necessary to effect suitable urethral occlusion. It will further be appreciated that the arcuate and bi-lobed geometries illustrated are exemplary only. Other geometries may be equally or more suitable.

Preferably, any of the described urethral occluders are designed to have a width less than the spacing of the external magnets, such as 14a. In this configuration, a urethral occluder does not interfere with the ability of the implant 12a and external 14a magnets to be attracted to one another. Preferably, the parallel sets of implant and external magnets enable a urethral occluder to be centered on the urethra 5. Preferably, the attractive force between implant and external magnets during placement, but prior to bodily contact, also creates a tactile sensation. This sensation may enable positioning of the external magnets relative to the implant magnets help to correctly align the occluder over the urethra.

Figure 10:
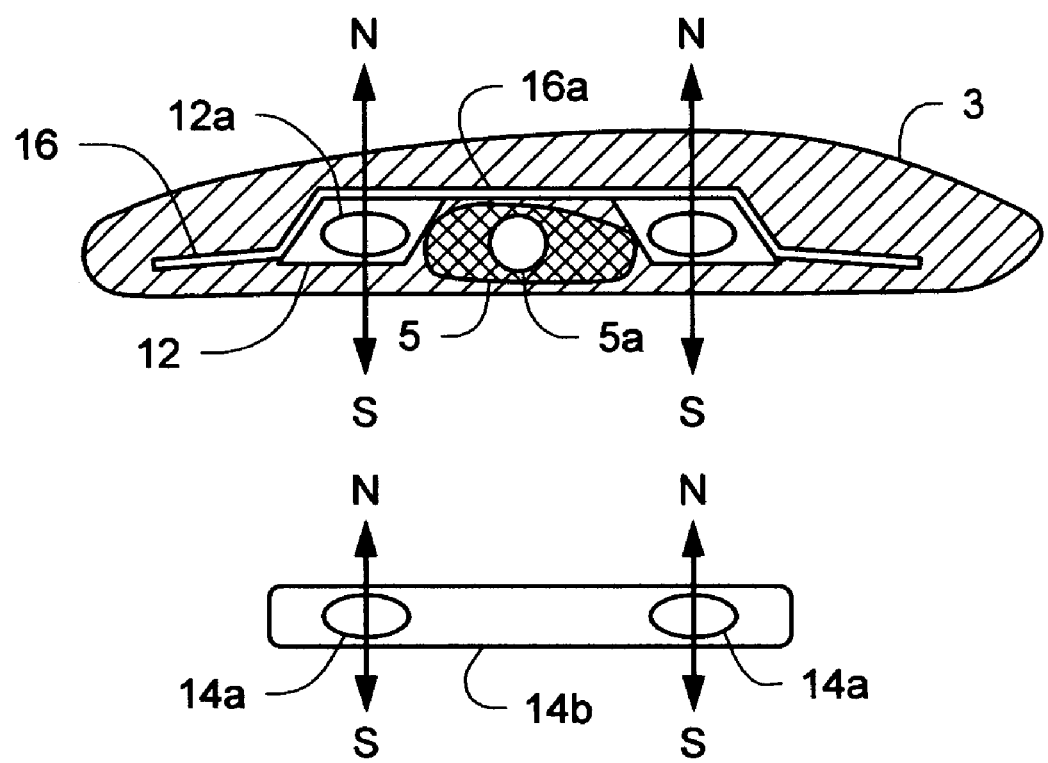
FIG. 10 represents yet another side view of the urethral occlusive assembly of FIG. 9A showing another embodiment for interaction between an implant component and an external component.

It is preferable that the implant magnets 12a repel one another. The magnetic poles of the implant magnets 12a are oriented to one another as shown in FIG. 10. This prevents attraction of the implant magnets 12a to one another across the urethra 5. If such attraction were to occur, the constant urethral pressure could erode or atrophy the urethral tissue. If the urethra 5 were to atrophy, the implant magnets 12a may be brought into closer proximity to one another. Exponentially increasing the attractive force between the implant magnets can increase tissue pressure to dangerous heights. Repulsion of the implant magnets 12a to one another also prevents a surgeon from having to intra-operatively separate the magnets to place them in the preferred position around the urethra.

Figure 9A:
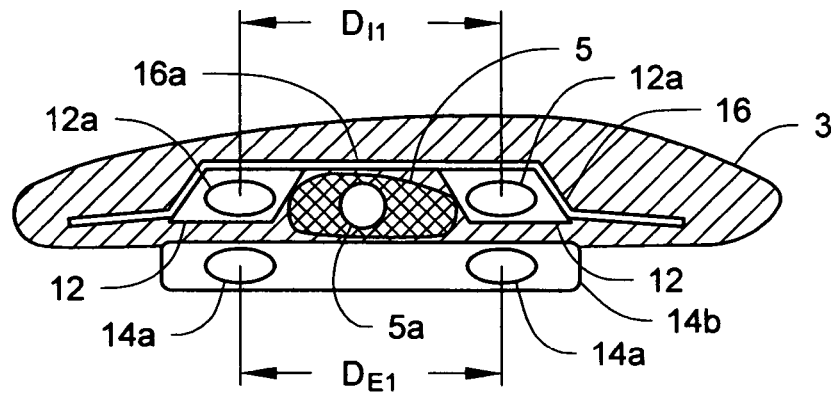
FIG. 9A represents an elevated side view of another embodiment of a urethral occlusive assembly. The assembly is shown before penile urethral compression.
Figure 9B:
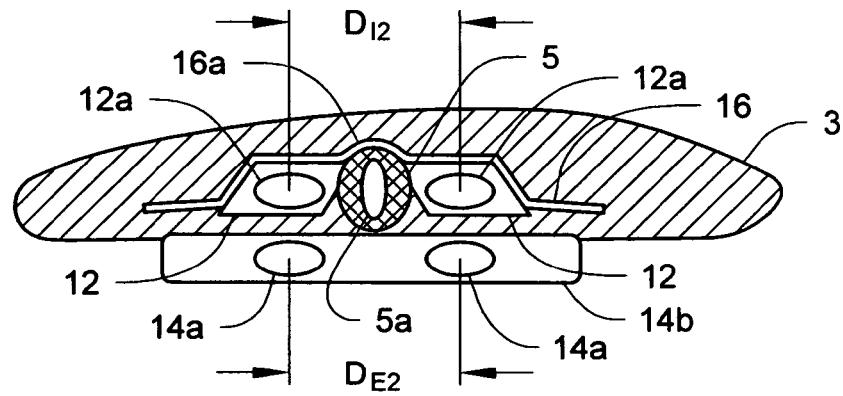
FIG. 9B represents an elevated side view of the urethral occlusive assembly of FIG. 9A showing the assembly during penile urethral compression.
Figure 9C:
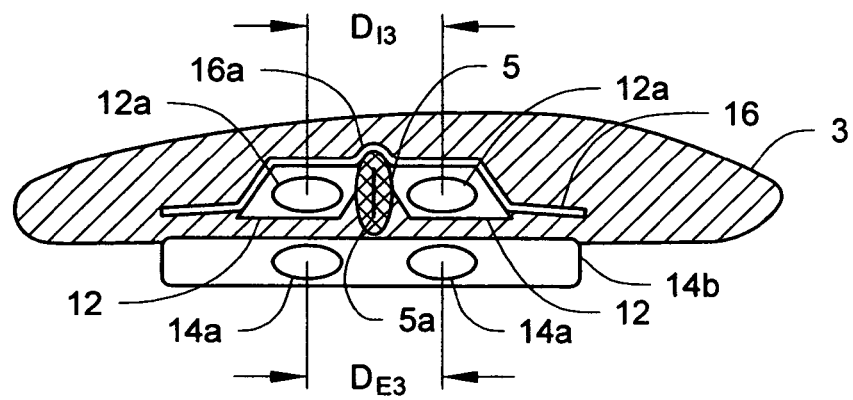
FIG. 9C represents yet another side view of the urethral occlusive assembly of FIG. 9A showing the assembly when the penile urethra is occluded.

FIGS. 9A–C illustrate another embodiment for modifying urethral compression in the urethral occlusive device 10. The degree of urethral compression may be varied by changing the separation distance between external magnets 14a. The external magnets 14a may be separated at varying distances, for example, decreasing distance $D_{E1}$ to $D_{E2}$ to $D_{E3}$. The decreasing distances adjust urethral compression, thereby varying the separation distance between the implant magnets 12a from $D_{I1}$, to $D_{I2}$ to $D_{I3}$. For example, distance $D_{I3}$ provides the highest urethral compression, where the urethra 5 is actively compressed by convergence of the implant supports 12. The urinary path 5a closes and the urethra 5 pushes against a flex point 16a of the flexible bridge member 16.

Figure 11:
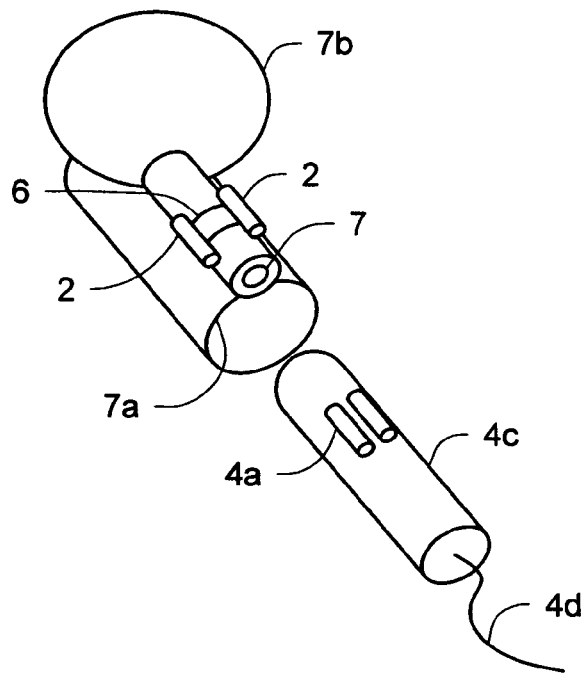
FIG. 11 represents an elevated perspective view of the urethral occlusive assembly of FIG. 1A showing the assembly for vaginal application and including one embodiment of a vaginal insertion member.

FIG. 11 illustrates a modified embodiment for vaginal urethral occlusion. Similar to FIG. 2, the implant component, including the implant magnets 2 and flexible bridge member 6, is disposed on a dorsal surface of a female urethra 7. The external magnets 4a may be brought into proximity with the implant magnet 2 at the anterior vaginal wall 7a by inserting an insertion member 4c. The insertion member 4c may resemble a tampon-like structure. A releasing member 4d may be connected at a distal end for removing the insertion member 4c. As one example only, the releasing member 4d may be a string.

Figure 12A:
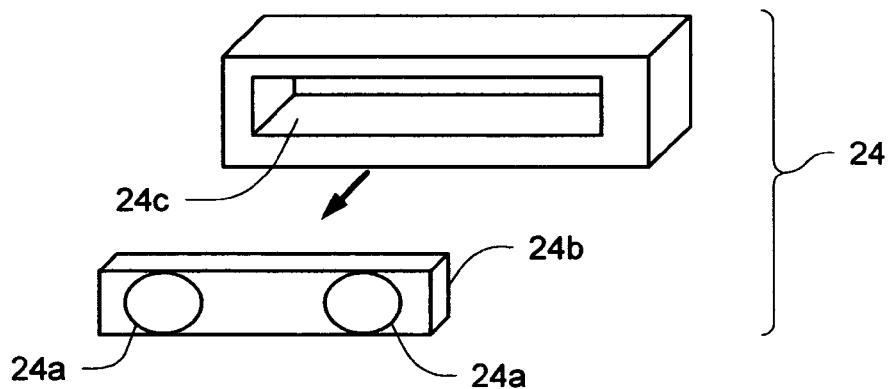
FIG. 12A represents an elevated exploded perspective view of another embodiment of an external component.
Figure 12B:
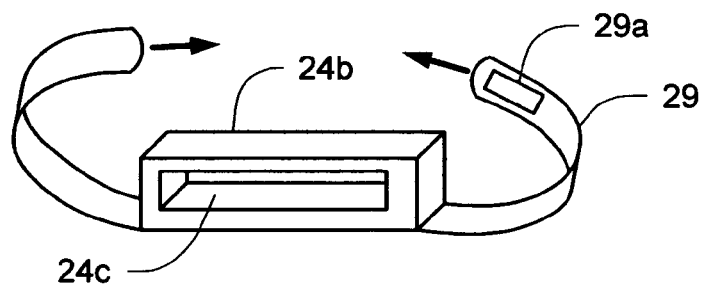
FIG. 12B represents an elevated perspective view of one embodiment of a sleeve for the external component of FIG. 12A showing an embodiment of an external securing member attached thereto.

FIG. 12A–B illustrate another embodiment for an external component 24 including external magnets 24a encased in a support plate 24b. A main body of the external component 24 defines a sleeve that is provided with a sleeve opening 24c. The external component 24 does not include a urethral occluder. The external component 24 may be held in place with an external securing member 29 and closure member 29a. The external securing member 29 and closure member 29a are similar to previously described members 19, 19b, and materials of manufacture are not further discussed.

Preferably, the external component defines a sleeve wall thickness of 0.085 inches between the attractive faces of the implant and external magnets. In this exemplary configuration, the opening of the sleeve assists in maintaining a constant separation distance and attractive or tissue force.

Figure 13A:
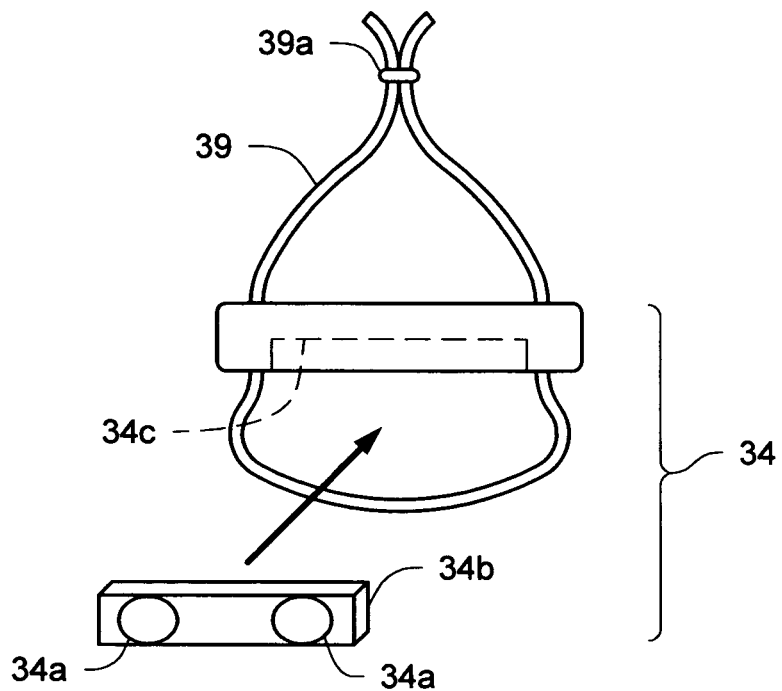
FIG. 13A represents an exploded view of yet another embodiment of an external component.
Figure 13B:
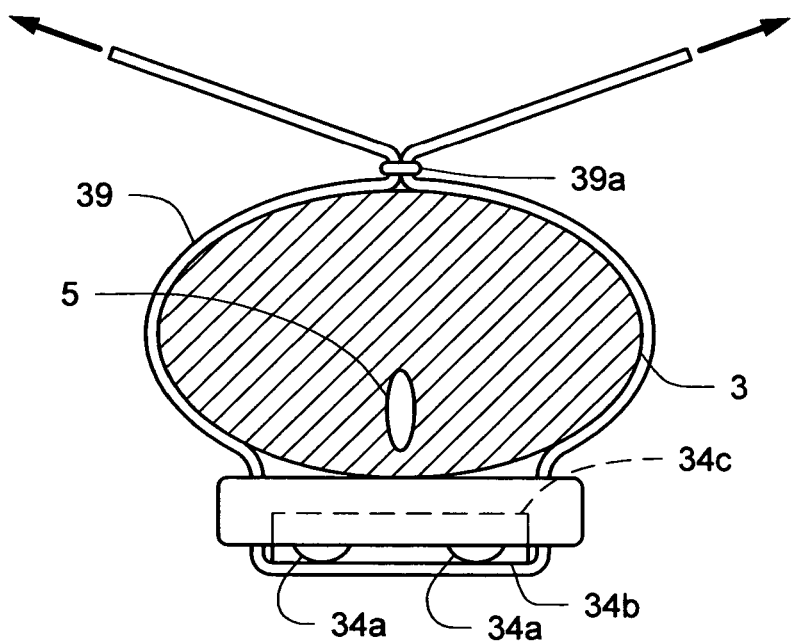
FIG. 13B represents a side view of the external component of FIG. 13A secured to a penis.

FIGS. 13A–B illustrate another embodiment for an external component 34. Similarly, external magnets 34a are encased in a support plate 34b. The main body of the external component defines a tray-like opening 34c (shown in phantom) rather than the previous sleeve opening. A modified external securing member 39 and modified closure member 39a are employed. The external securing member 39 may be, but is not limited to a strap or band-like or tie-like structure thread through the main body of the external component. The closure member provides a friction closure that employs an o-ring.

In this configuration, the external securing member 39 is pulled through the main body to hold the external magnets 34a and support plate 34b tightly within the opening 34c. The penis 3 is then placed through the external securing member 39. The external 34a and implant magnets (not shown) may be aligned. As indicated by the arrow directional in FIG. 13B, two free ends of the securing member 39 are pulled apart, forcing the closure member 39a downward along the arms of the securing member 39 toward the penis 3. Once the penis 3 is cinched within the securing member 39, frictional forces between the closure member 39a and securing member 39 prevent loosening.

As detailed above, a wide variety of magnetic materials and geometries may be used for the reusable external magnet. As one example only, a pair of grade 32 NdFeB rectangles, 0.10 inches×0.27 inches×0.72 inches magnets may be employed. Preferably, these magnets are magnetized across the 0.10 inch dimension and have the strength necessary to attract and hold the implant magnets.

Implant experiments have indicated that misalignment of the implant magnets may occur. Application of a rigid external magnet may cause localized pressure zones that are excessively high, and can result in tissue necrosis.

Figure 14A:
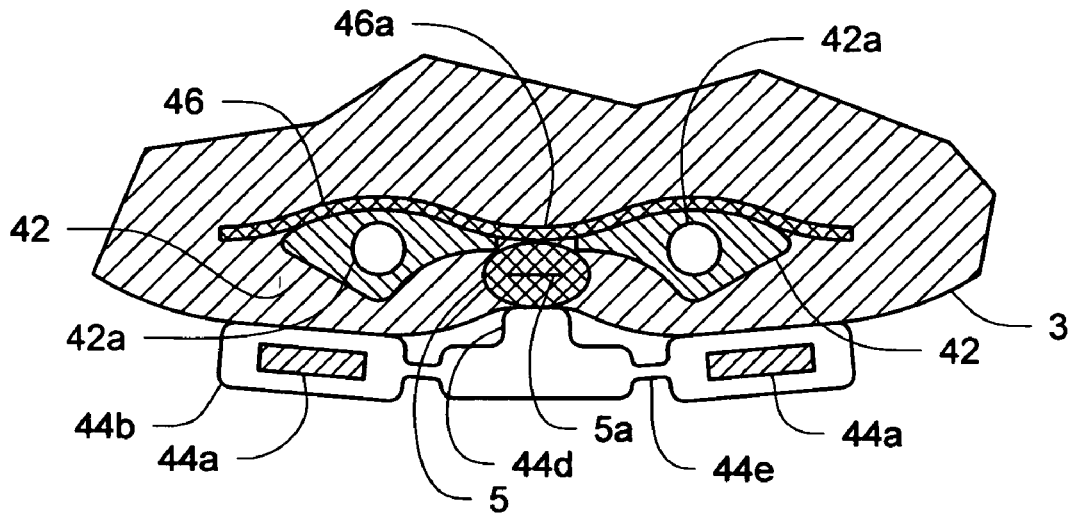
FIG. 14A represents a side partial sectional view of yet another embodiment of a urethral occlusive assembly showing the assembly in a position where the urethra is compressed.
Figure 14B:
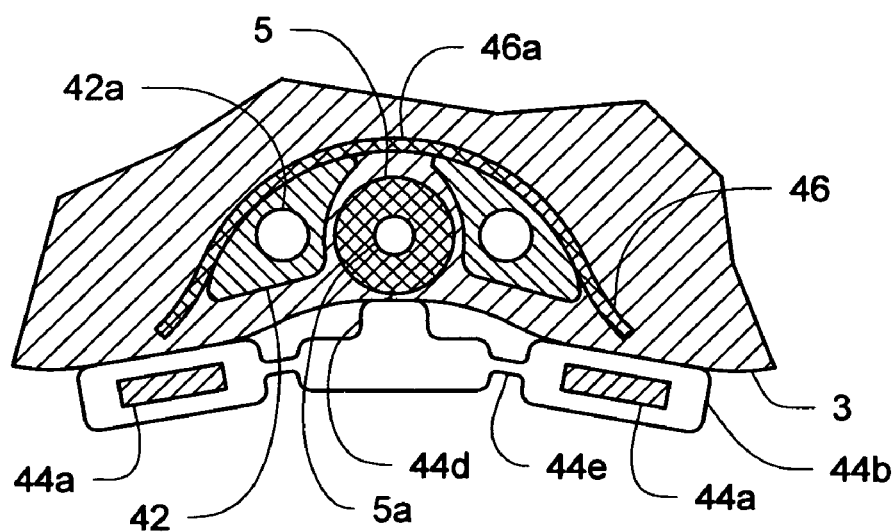
FIG. 14B represents a side partial sectional view of the urethral occlusive assembly of FIG. 14A showing the assembly in a position where the urethra is not compressed.

FIGS. 14A–B show another embodiment for an external component 40 having a flexible web. The flexible web may prevent implant misalignment and help preserve skin integrity, while providing sufficient attractive strength between the external magnets and implant magnets of an implant component.

The magnet support 44b includes a flexible web portion 44e disposed along the body thereof. The flexible web 44e enables the magnet support 44b to articulate on the outer surface of the penis 3. As shown in FIGS. 14A–B, the flexible web 44e allows the external magnet 44a to align with each implant support 42 and implant magnet 42a. Assuring that flat faces of the implant and external magnets 42a, 44a are parallel, compressive loads may be distributed over a larger tissue surface area, thereby reducing excessive tissue pressure. The urethral occluder 44d may then actively compress the urethra 5 against the flexible bridge member 46 and flex point 46a.

Tissue pressure can be determined by the surface of contact between the implant and external magnets including any air gap between the implant and external magnets. Tissue thickness determines the effective air gap and may vary due to anatomical differences from user to user, difference in tissue compressibility and degree of capsular formation around the implant. To maintain an appropriate tissue pressure (approximately $\leq 60$ mmHg), the air gap may be altered to fit a particular patient by measuring the force required to remove the external magnet from the penis, calculating the tissue pressure and selecting a removable spacer for disposal on the external support and magnet.

Figure 16:
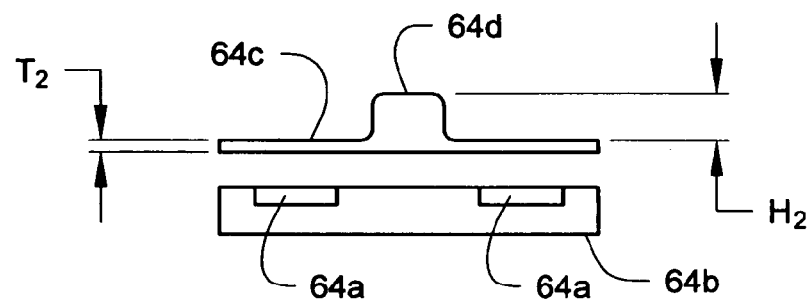
FIG. 16 represents an elevated side view of yet another embodiment for an external component.

FIG. 16 illustrates one embodiment of a removable spacer 64c, of which dimensions may be varied as necessary for use. The removable spacer 64c is disposed over the external magnets 64a and an external magnet support 64b. The "X" dimension represents a thickness T2 that may be available in 0.020 inch increments. The "Y" dimension defines a height H2 of the occlusive bump 64d that may be available in 0.020 inch increments to allow modification of urethral pressure. It will be appreciated, however, that these measurements are exemplary only, as other dimensions and increments may be equally or more suitable.

Magnetic field interference among multiple implant and topically applied magnets might limit the ability of the implant component to squeeze the urethra 5 and close the urinary pathway 5a, previously described, for instance, in FIGS. 9A–B.

Figure 15A:
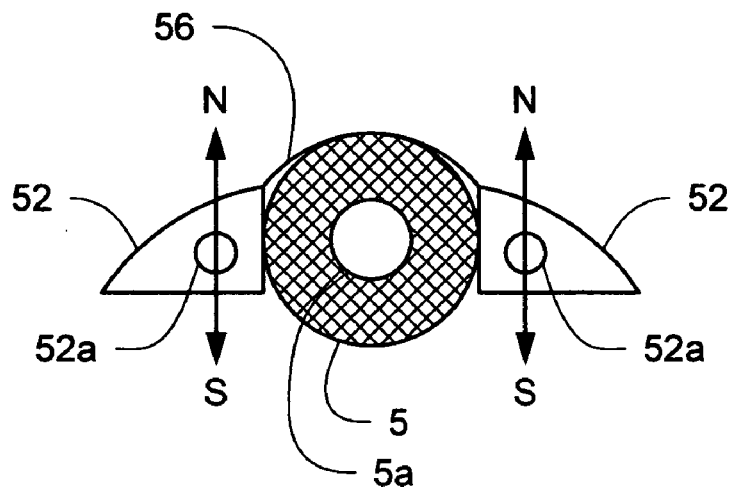
FIG. 15A represents a side partial sectional view of yet another embodiment of a urethral occlusive assembly showing the assembly in a position where the urethra is not compressed.
Figure 15B:
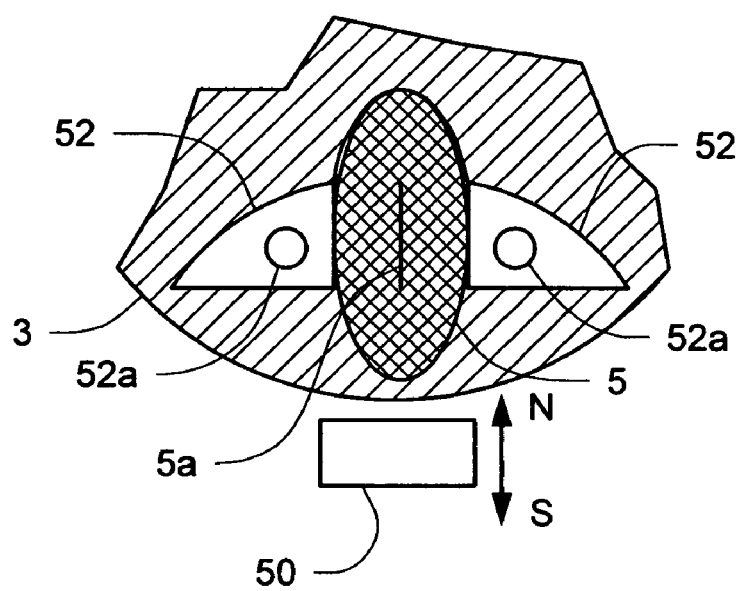
FIG. 15B represents a side partial sectional view of the urethral occlusive assembly of FIG. 15A showing the assembly in a position where the urethra is compressed.

FIGS. 15A–B illustrate an embodiment for an external component including a single topically applied magnet. In this embodiment, the external component 50 includes only one external magnet. This single magnet can obviate some of the field interferences. In this configuration, active compression by the implant supports 52 through the implant magnets 52a may be more positive and reliable. The implant component as described in FIGS. 9A–C is similar to the implant component shown in FIGS. 15A–B. An implant support 52 and implant magnets 52a are provided with a flexible bridge member 56. Preferably, the external magnet is a reusable magnet as the previously described.

It will be appreciated that the single topically applied magnet may be adapted to fit with any of the previously described external magnet supports without an occluder. It will be appreciated that the single magnet may be adapted for use with any of the external securing members previously described.

Figure 17A:
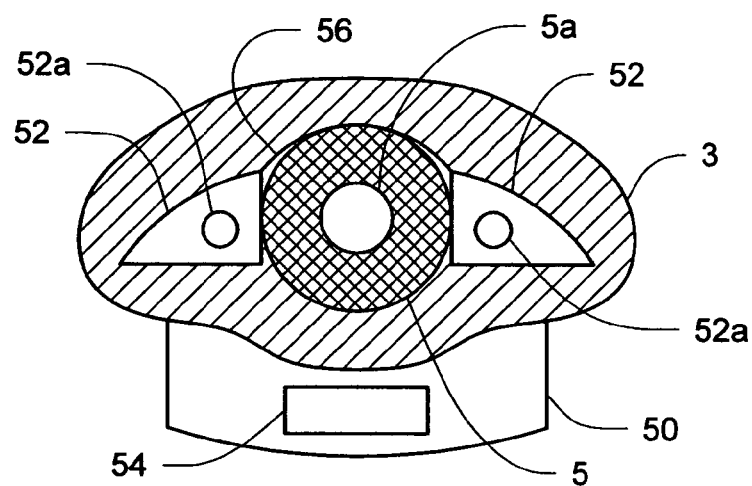
FIG. 17A represents a side partial sectional view of yet another embodiment of a urethral occlusive assembly showing the assembly in a position where the urethra is not compressed.
Figure 17B:
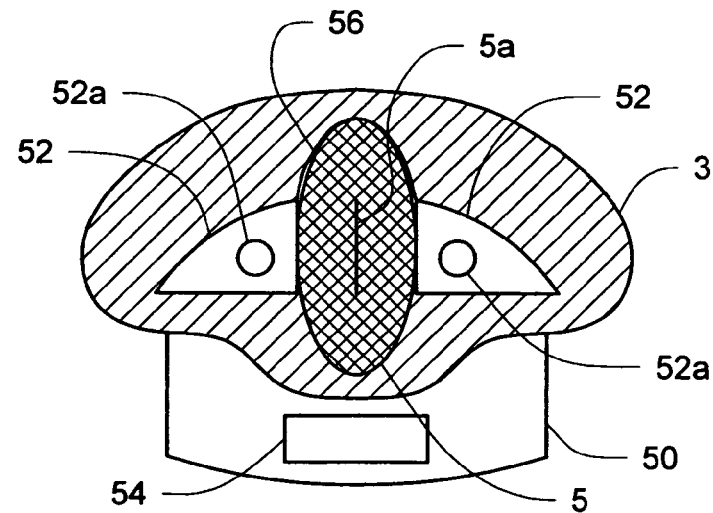
FIG. 17B represents a side partial sectional view of the urethral occlusive assembly of FIG. 17A showing the assembly in a position where the urethra is compressed.

Several methods may be employed to vary the degree of urethral compression provided by the urethral occlusive assembly as disclosed in any of the previously described embodiments. By varying the urethral compression, a physician can provide the degree of urinary continence appropriate for individual patients. As shown in FIGS. 17A–B, the magnet strength may be increased to increase urethral compression, where a stronger magnet may be employed rather than a weaker one or vice versa for a decrease in urethral compression. In this configuration, external magnet 54 may be replaced by magnets of differing strength as desired.

Figure 18A:
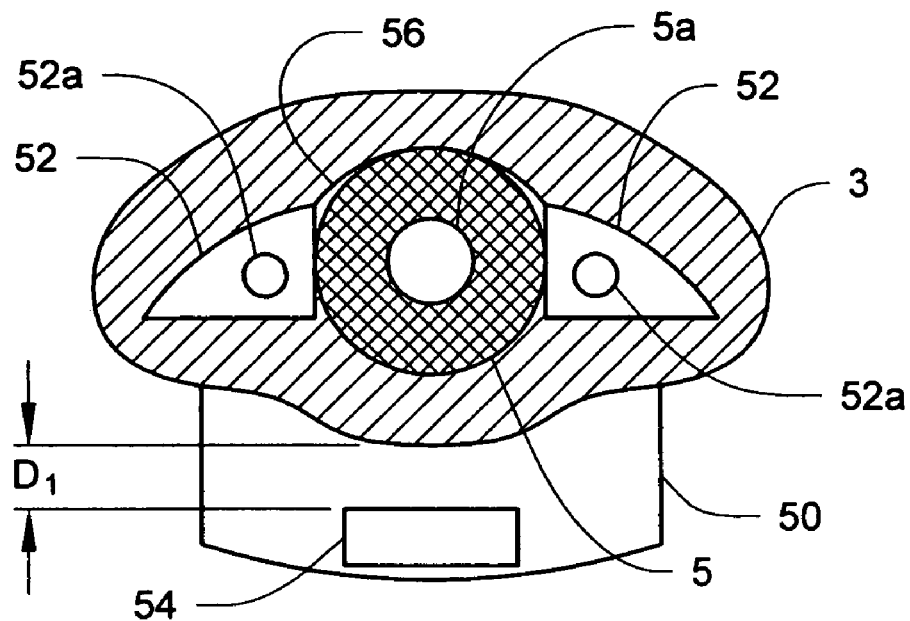
FIG. 18A represents a side partial sectional view of yet another embodiment of a urethral occlusive assembly showing the assembly in a position where the urethra is not compressed.
Figure 18B:
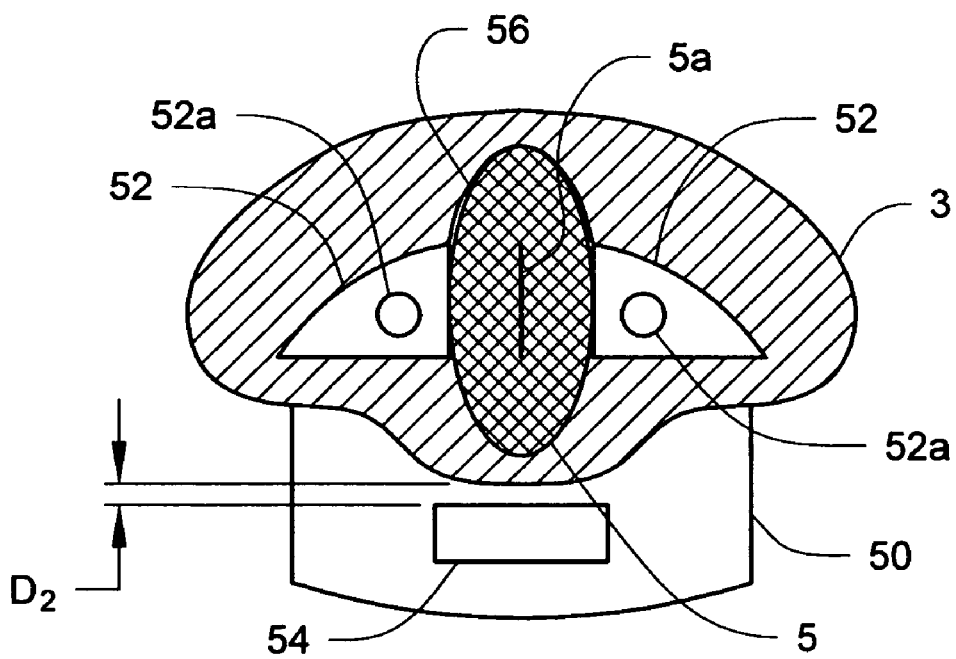
FIG. 18B represents a side partial sectional view of the urethral occlusive assembly of FIG. 18A showing the assembly in a position where the urethra is compressed.

FIGS. 18A–B illustrate an embodiment for varying urethral compression by varying the separation distance D. FIG. 18A illustrates an external magnet 54 contained within the external component 50 having a separation distance D1 from the outer surface of the penis 3. In this configuration, urethral pressure can be increased, where the implant supports 52 actively converge to compress the urethra 5 against the flexible bridge member 56. Differently, urethral compression may be increased when the external magnet 54 is disposed within the external component 50 at a reduced separation distance D2. Thereby, the urethral compression may be decreased.

Thus, the separation distance between the top surface of the external magnet and penile skin may be increased/decreased to effectively increase/decrease the magnetic attractive strength between the implant and external magnets 52a, 54a. The varying separation distances accordingly effect change in the urethral compression.

It will be appreciated that the separation distances and magnetic strengths may vary as desired for application of the urethral occlusive assembly. As illustrated in FIGS. 17A–18B, the magnetic strength and separation distance principles are shown with respect to a urethral occlusive device employing a single external magnet. It will be appreciated, however, that such principles are not limited to this embodiment, and may be suitably adapted to any of the previously described embodiments.

It has been noted in some patient trials, that an expansion space or recess is desirable on the external magnet support of the external component. Such a recess enables expansion of the urethra and outer penile skin into the recess, when the urethra is actively compressed by the implant supports and magnets of the implant component.

Figure 19A:
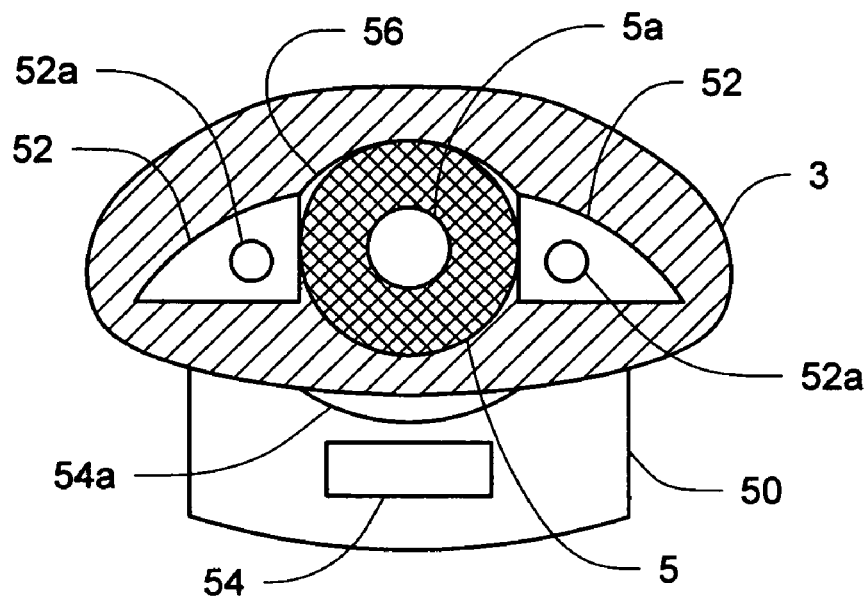
FIG. 19A represents a side partial sectional view of yet another embodiment of a urethral occlusive assembly showing the assembly in a position where the urethra is not compressed.
Figure 19B:
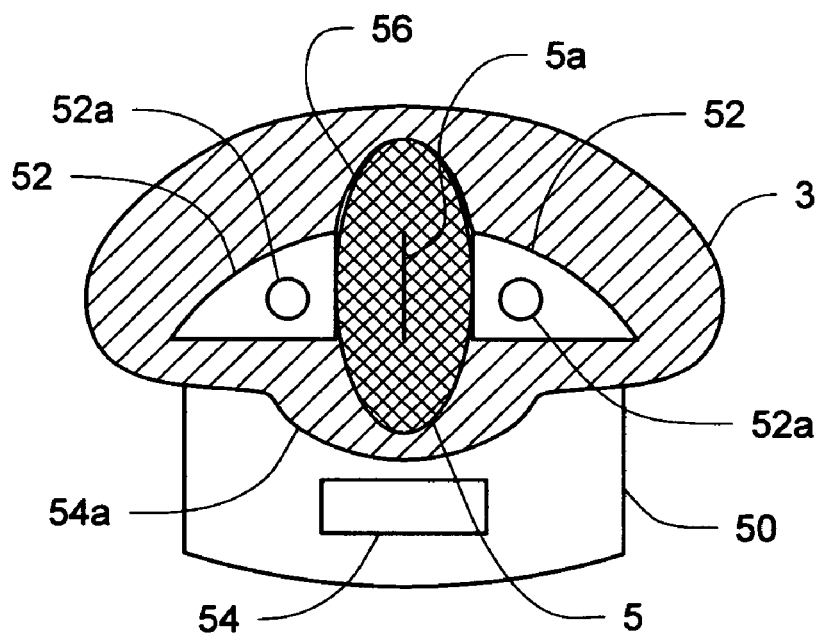
FIG. 19B represents a side partial sectional view of the urethral occlusive assembly of FIG. 19A showing the assembly in a position where the urethra is compressed.

FIGS. 19A–B illustrate a recess 54a disposed on the external magnet support of the external component. When the implant supports 52 and implant magnets 52a actively compress the urethra 5 to close the urinary pathway 5a, the urethra 5 and outer skin of the penis 3 may move into the recess 54a.

In this configuration, compression of the urethra may be accomplished without undue pressure against the penile tissue, thereby preventing tissue necrosis. It will be appreciated that a recess, as recess 54a, may be employed with any of the previous embodiments not employing an occluding bump on the external component. For example, a recess may be employed when two external magnets are used to compress the urethra (FIGS. 9A–C).

It will be appreciated that an embodiment may be employed where magnets are not necessary to magnify the occlusive load on the urethra to prevent urine leakage.

Figure 20A:
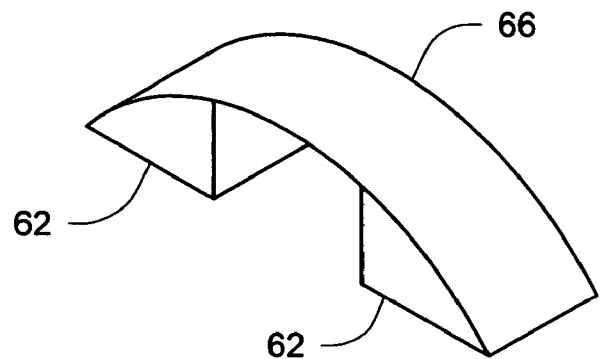
FIG. 20A represents an elevated perspective view of yet another embodiment of an implant component.
Figure 20B:
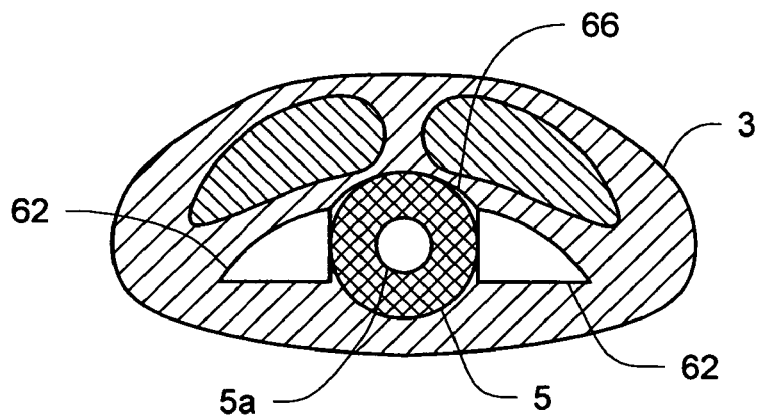
FIG. 20B represents a side partial sectional view of yet another embodiment for a urethral occlusive assembly showing the assembly in a position where the urethra is not compressed and employing the implant component of FIG. 20A.
Figure 20C:
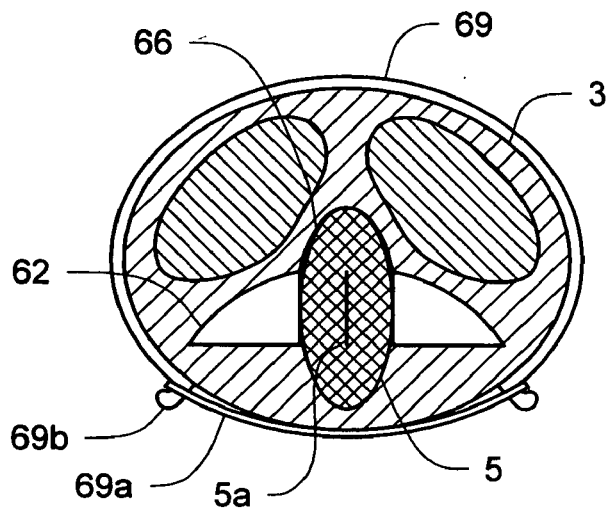
FIG. 20C represents a side partial sectional view of the urethral occlusive assembly of FIG. 20B showing the assembly in a position where the urethra is compressed.

FIGS. 20A–C illustrate another embodiment for a urethral occlusive assembly that does not employ magnets. An implant component defines a semi-rigid implant having a flexible bridge member 66 with two implant supports 62 at each end. The implant supports 62 may be a semi-rigid silicone material and the flexible bridge member 66 may be a reinforced silicone backing material. Preferably, the implant supports 62 are semi-rigid silicone capsules as previously described without any implant magnets residing therein. It will be appreciated that other materials may be employed that are equally or more suitable. As an example only, the implant supports 62 and flexible bridge 66 may be produced of materials described in the previously detailed embodiments.

As shown in FIG. 20C, an external securing member 69 may be employed as the external component. Preferably, the external securing member 69 may be an external strap placed around the penis 3 to compress the penile tissue around the outer penile circumference. The external securing member 69 may include a closure member 69a secured to hook portions 69b to thereby secure the member 69 to the penis 3. Preferably, the closure member 69a is an elastic biasing band. However, it will be appreciated that an elastic biasing band is merely exemplary. Other forms of a closure member may be employed and may be equally or more suitable. This compression is transmitted or imparted to the implant supports 62. The implant supports 62 actively concentrate a load on the urethra 5 as a result of the implant supports' non-viscous elastic nature. This non-magnetic action can improve efficiency of the urethral occlusive assembly. Lower external penile pressures than that of the magnetically compressed embodiments may be applied to effect urinary continence.

The urethral occlusive assembly provides several features and advantages as mentioned above. For example, urethral compression may be adjusted without additional surgery to accommodate changing degrees of incontinence. This may be accomplished through application of external magnets of varying strengths or the selection of different urethral occluder geometries.

The urethral occlusive assembly described provides the ability to remove the external magnet and hence the occlusive pressure from urethra and penis periodically, so as to minimize urethral atrophy and erosion.

The urethral occlusive assembly described provides removal and re-application of the external magnet by the user, so that voiding urine from the body is a simple, convenient procedure. The need to locate and pump an implanted component is eliminated. Further, there is no abdominal straining required to void urine, as typically required with urethral slings.

The urethral occlusive assembly described provides a simple, one-piece, implantable component not prone to wear and subsequent fluid leakage. The urethral occlusive assembly may be implanted using a single implant incision with uncomplicated penile urethral dissection.

The above specification provides a complete description of the composition, manufacture and use of the improved urethral occlusive assembly in accordance with the principles of the present invention. Since many embodiments of the invention can be made without departing from the spirit and scope of the invention, the invention resides in the claims hereinafter appended.

The invention claimed is:

1. A urethral occlusive assembly, comprising:
an implant component, the implant component including a flexible bridge member having two opposed implant supports, each of the implant supports including an implant magnet, the implant component is adapted for being implanted in a patient about a dorsal surface of a urethra, such that the flexible bridge is disposed on the dorsal surface of the urethra and the implant magnets are oppositely disposed of each other on the urethra; and
an external component, the external component including at least one external magnet, the at least one external magnet being magnetically attracted to the implant magnets, the external component is adapted for being disposed proximate the urethra and outside of the patient,
the external component and the implant component operatively communicating with each other by imparting magnetic attraction with one another when the external component is disposed proximate the urethra, and by releasing magnetic attraction with one another when the external component is not disposed proximate the urethra,
wherein, when the implant component and the external component are magnetically attracted, one of the implant component or the external component is adapted for transmitting a compressive load on the urethra and thereby compressing the urethra to effect urinary continence.

2. The assembly according to claim 1, wherein the implant magnets are respectively encased within the implant supports.

3. The assembly according to claim 1, wherein the external component including an external securing member connected with the at least one external magnet, the external securing member being adapted for holding the at least one external magnet proximate the urethra.

4. The assembly according to claim 1, wherein the external component including an external urethral occluding member, the occluding member being adapted for actively transmitting a localized compressive load on the urethra to compress the urethra against the flexible bridge member.

5. The assembly according to claim 4, wherein the urethral occluding member defining a height and a width dimension, the height and width being constructed with an arcuate shape.

6. The assembly according to claim 4, wherein the urethral occluding member defining a height and a width dimension, the height and width being constructed with a bi-lobed shape.

7. The assembly according to claim 1, wherein the external component including a magnet support for supporting the at least one external magnet.

8. The assembly according to claim 7, wherein the magnet support and the at least one external magnet being housed within a sleeve opening in a main body of the external component.

9. The assembly according to claim 7, wherein the external component including a flexible web portion, the flexible web portion being disposed along a body of the magnet support, the flexible web portion being adapted for enabling the magnet support to externally articulate on an outer tissue proximate the urethra.

10. The assembly according to claim 7, wherein the magnet support including a removable spacer disposed upon the external magnet, the removable spacer including a varying thickness for varying a separation distance between the at least one external magnet and the implant magnets.

11. The assembly according to claim 7, wherein the at least one external magnet being disposed within the magnet support at varying separation distances from the implant magnets.

12. The assembly according to claim 1, wherein the the at least one external magnet including a pair of external magnets, the pair of external magnets are adapted to be disposed proximate the urethra and outside the patient, and when the pair of external magnets is disposed proximate the urethra, one of the external magnets being magnetically attracted to one of the implant magnets and the other of the external magnets being magnetically attracted to the other of the implant magnets.

13. The assembly according to claim 12, wherein the pair of external magnets including a spacing therebetween, the spacing being increasingly or decreasingly variable to respectively decrease or increase urethral compression, the implant magnets enabling the implant supports to actively compress the urethra when the implant magnets are attracted to the pair of external magnets.

14. The assembly according to claim 1, wherein the external component including a support with a recess being disposed on an outer surface of the support, the recess is adapted to be disposed proximate the urethra and outside the patient, whereby when the urethra is compressed, the recess enabling the urethra and skin tissue of the patient to expand into a space of the recess.

15. The assembly according to claim 1, wherein the flexible bridge member defining a flex point, the flex point being disposed at a leading edge of the flexible bridge member.

16. A method for preventing urinary leakage, comprising:
providing a urethral occlusive assembly including an implant component and an external component, the implant component including a flexible bridge member having two opposed implant supports, each of the implant supports including an implant magnet, the external component including at least one magnet, the at least one magnet of the external component being magnetically attracted to the implant magnets;

implanting the implant component inside a patient about a dorsal surface of a urethra;

disposing the external component proximate the urethra and outside of the patient;

enabling communication between the implant component and the external component, the step of enabling communication including imparting magnetic attraction between the implant component and the external component when the external component is disposed proximate the urethra, and including releasing magnetic attraction between the implant component and the external component when the external component is not disposed proximate the urethra; and compressing the urethra when the implant component and the external component are magnetically attracted, the step of compressing the urethra includes one of the implant component or the external component actively compressing the urethra;

wherein the urethra is compressed to effect urinary continence.

17. The method according to claim 16, wherein the step of compressing the urethra includes the external component imparting a localized external compressive load on the urethra to actively compress the urethra against the flexible bridge member.

18. The method according to claim 16, wherein the step of compressing the urethra includes converging the implant supports to actively compress the urethra, converging the implant supports including laterally compressing the urethra.

19. A male urethral occlusive assembly, comprising:
an implant component, the implant component including a flexible bridge member having two opposed implant supports, the implant component is adapted to be implanted in a male patient about a dorsal surface of a urethra, such that the flexible bridge is disposed on the dorsal surface of the urethra and the implant supports are oppositely disposed of each other on the urethra; and an external component, the external component is adapted to be disposed around a penis of the patient, the external component operatively communicating with the implant component to transmit a compressive load on the implant supports when the external component is compressed;

wherein, when the external component transmits a compression on the implant component, the implant supports may be compressed and are adapted for actively concentrating a load an the urethra to effect urinary continence.

20. The assembly according to claim 19, wherein the implant component defining implant supports being non-magnetic.

* * * * *